(12) United States Patent
Skatter et al.

(10) Patent No.: US 9,618,462 B2
(45) Date of Patent: Apr. 11, 2017

(54) SYSTEMS AND METHODS FOR IMAGING AND DETERMINING A SIGNATURE OF AN OBJECT

(71) Applicant: Morpho Detection, LLC, Newark, CA (US)

(72) Inventors: Sondre Skatter, Oakland, CA (US); Samit Kumar Basu, Fremont, CA (US)

(73) Assignee: MORPHO DETECTION, LLC, Newark, CA (US)

( * ) Notice: Subject to any disclaimer, the term of this patent is extended or adjusted under 35 U.S.C. 154(b) by 289 days.

(21) Appl. No.: 14/571,438

(22) Filed: Dec. 16, 2014

(65) Prior Publication Data

US 2016/0169817 A1   Jun. 16, 2016

(51) Int. Cl.
| | |
|---|---|
| *G01N 23/20* | (2006.01) |
| *G01N 23/04* | (2006.01) |
| *G06T 7/00* | (2017.01) |
| *A61B 6/06* | (2006.01) |
| *G01V 5/00* | (2006.01) |
| *A61B 6/03* | (2006.01) |
| *G21K 1/02* | (2006.01) |
| *A61B 6/00* | (2006.01) |

(52) U.S. Cl.
CPC ....... *G01N 23/20075* (2013.01); *A61B 6/032* (2013.01); *A61B 6/06* (2013.01); *A61B 6/5282* (2013.01); *G01N 23/046* (2013.01); *G01V 5/00* (2013.01); *G06T 7/004* (2013.01); *G06T 7/0012* (2013.01); *A61B 6/5205* (2013.01); *G06T 2207/10081* (2013.01); *G21K 1/02* (2013.01)

(58) Field of Classification Search
CPC .......... A61B 6/032; A61B 6/542; A61B 6/06; A61B 6/4035; A61B 6/405; G01N 23/046; G01N 2021/8472; G01N 2223/1016
See application file for complete search history.

(56) References Cited

U.S. PATENT DOCUMENTS

| | | | | |
|---|---|---|---|---|
| 6,385,278 | B1 * | 5/2002 | Hsieh | A61B 6/032 378/15 |
| 2004/0008817 | A1 * | 1/2004 | Nagai | A61B 6/032 378/98.5 |
| 2015/0313569 | A1 * | 11/2015 | Stevens | A61B 6/032 378/8 |

* cited by examiner

*Primary Examiner* — Hoon Song
(74) *Attorney, Agent, or Firm* — Armstrong Teasdale LLP

(57) ABSTRACT

An X-ray CT scanner for imaging an object is provided. The scanner includes an X-ray emitter configured to emit X-ray beams, a detector array including a plurality of detector elements, and a precollimator positioned between the X-ray emitter and the object, the precollimator configured to prevent the emitted X-ray beams from being directly incident on a first subset of the plurality of detector elements, and allow the emitted X-ray beams to be directly incident on a second subset of said plurality of detector elements. A processing device communicatively coupled to the detector array is configured to determine a signature of the object based on a first set of data acquired using the first subset of the plurality of detector elements, and tomographically reconstruct an image of the object based on a second set of data acquired using the second subset of said plurality of detector elements.

20 Claims, 10 Drawing Sheets

SYSTEMS AND METHODS FOR IMAGING AND DETERMINING A SIGNATURE OF AN OBJECT

BACKGROUND

The embodiments described herein relate generally to imaging objects, and more particularly, to imaging systems for reconstructing an image of an object and determining a signature of the object.

In some computed tomography (CT) imaging system configurations, an x-ray source projects a fan-shaped beam which is collimated to lie within an X-Y plane of a Cartesian coordinate system and generally referred to as an "imaging plane". The x-ray beam passes through an object being imaged. The beam, after being attenuated by the object, impinges upon an array of radiation detectors. The intensity of the attenuated radiation beam received at the detector array is dependent upon the attenuation of the x-ray beam by the object. Each detector element of the array produces a separate electrical signal that is a measurement of the beam intensity at each detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray fan beam intersects the object constantly changes. A group of x-ray attenuation measurements (e.g., projection data) from the detector array at one gantry angle may be referred to as a "view". A "scan" of the object comprises a set of views made at different gantry angles, or view angles, during one or more revolutions of the x-ray source and detector about the object or patient being imaged.

Many modern CT systems are helical scanners (also known as spiral scanners), in which the scanned object is continually moved while the projection data is being acquired. The path of the x-ray source describes a helix with respect to the scanned object. Most helical scanners have multiple rows of detectors, and the x-ray fan is collimated into a cone to illuminate the entire array of detectors. The angle between the x-ray source and the first and last detector rows is referred to as the "cone angle".

At least some known CT systems are able to reconstruct an image of the scanned object, but are unable to determine a composition of the object. Accordingly, although the shape and dimensions of the object may be ascertainable using at least some known CT systems, the composition may be indeterminable. Determining the composition of a given object, in addition to the shape and dimensions of the object, would assist in determining whether or not an object is contraband.

BRIEF SUMMARY

In one aspect, an X-ray CT scanner for imaging an object is provided. The X-ray CT scanner includes an X-ray emitter configured to emit X-ray beams towards the object, a detector array positioned opposite the X-ray emitter and including a plurality of detector elements, and a precollimator positioned between the X-ray emitter and the object, the precollimator configured to prevent, using at least one blocking portion, the emitted X-ray beams from being directly incident on a first subset of the plurality of detector elements, and allow the emitted X-ray beams to be directly incident on a second subset of said plurality of detector elements. The X-ray CT scanner further includes a processing device communicatively coupled to the detector array, the processing device configured to determine a signature of the object based on a first set of data acquired using the first subset of the plurality of detector elements, and tomographically reconstruct an image of the object based on a second set of data acquired using the second subset of said plurality of detector elements.

In another aspect, a method for imaging an object is provided. The method includes positioning the object between an X-ray emitter and a detector array that includes a plurality of detector elements, emitting X-ray beams towards the object from the X-ray emitter, preventing, using a precollimator including at least one blocking portion, the emitted X-ray beams from being directly incident on a first subset of the plurality of detector elements, allowing the emitted X-ray beams to be directly incident on a second subset of the plurality of detector elements, determining, using a processing device communicatively coupled to the detector array, a signature of the object based on a first set of data acquired using the first subset of the plurality of detector elements, and tomographically reconstructing, using the processing device, an image of the object based on a second set of data acquired using the second subset of the plurality of detector elements.

In yet another aspect, a method of assembling an X-ray CT scanner for imaging an object is provided. The method includes positioning an X-ray emitter opposite a detector array that includes a plurality of detector elements, the X-ray emitter configured to emit X-ray beams towards the object, and positioning a precollimator between the X-ray emitter and the object, the precollimator including at least one blocking portion configured to prevent the emitted X-ray beams from being directly incident on a first subset of the plurality of detector elements, and allow the emitted X-ray beams to be directly incident on a second subset of the plurality of detector elements. The method further includes communicatively coupling a processing device to the detector array, the processing device configured to determine a signature of the object based on a first set of data acquired using the first subset of the plurality of detector elements, and tomographically reconstruct an image of the object based on a second set of data acquired using the second subset of the plurality of detector elements.

DETAILED DESCRIPTION

The embodiments described herein provide a CT imaging system that is capable of reconstructing an image of an object and determining a signature, or composition, of the object. By determining a signature in addition to imaging the object, contraband detection may be improved and false alarms may be reduced. As used herein, the "signature" may be a molecular signature (e.g., if the object is composed of a single type of molecule) or may be a more general signature that represents a mix of the molecular signatures corresponding to different types of molecules that constitute the object.

As used herein, raw data refers to the actual data value read from a detector. The raw data depends on the x-ray intensity at the detector, the gain of the detector, and any bias (offset) that is added to the detector value. Furthermore and as also used herein, offset data, gain data, sample data, x-ray intensity, normalized data, converted data, x-ray source position, reconstruction circle, and reconstruction volume are as defined as follows:

Offset data: Raw data measurements collected with the x-ray source off.

Gain data: Raw data measurements collected with the x-ray source on, but with no sample objects in the field of view other than permanently installed objects such as the conveyor belt.

Sample data: Raw data measurements collected with the x-ray source on and a sample object in the field of view.

X-ray intensity: The intensity of the x-ray at each detector. X-ray intensity can be computed as K1*(Sample-Offset)/(Gain-Offset), where K1 is a calibration constant.

Normalized data: A measure of the attenuation of an x-ray beam as it travels through an object. Normalized data can be computed as K2*log((Gain-Offset)/(Sample-Offset), where K2 is a calibration constant and log( ) is the natural logarithm.

Converted data: Any useful representation of the scan data that may be used for a projection image. In the exemplary embodiment, converted data represents normalized data, but other representations (e.g., sample data, x-ray intensity) may be used.

X-ray source position: The gantry may make several complete rotations during acquisition, creating a spiral trajectory of the x-ray source when viewed with respect to the moving scanned object. X-ray source position in this discussion refers to a single point in the spiral trajectory.

Reconstruction Circle: A circle defined by the x-ray fan as the x-ray tube rotates around an object. For accurate CT reconstruction, an object must be entirely within the reconstruction circle.

Reconstruction Volume: A cylinder in the scanned object's coordinates defined by the reconstruction circle and the length of the bag for which there is sufficient data to reconstruct.

Figure 1:
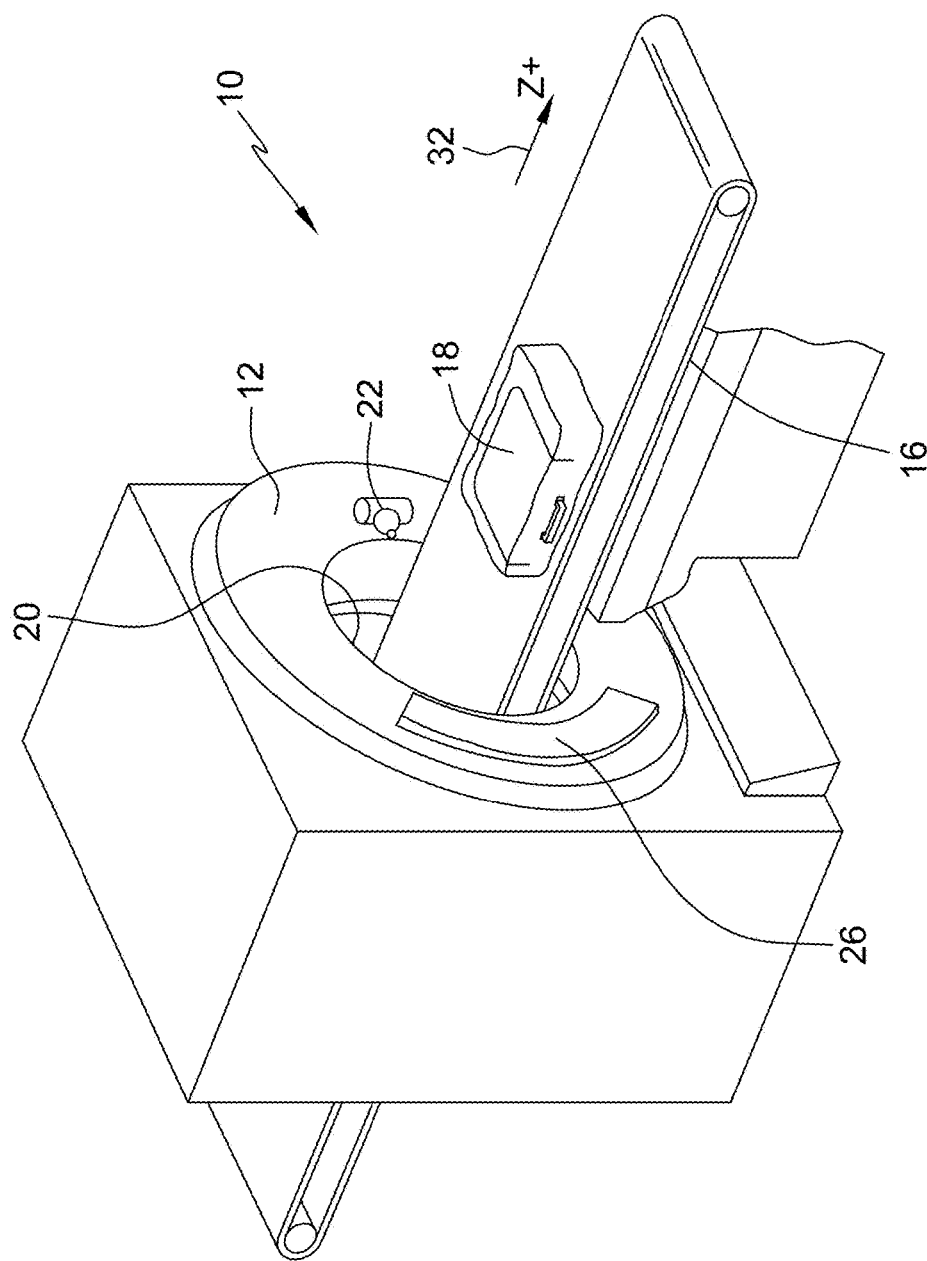
FIG. 1 is a perspective view of an exemplary CT imaging system.
Figure 2:
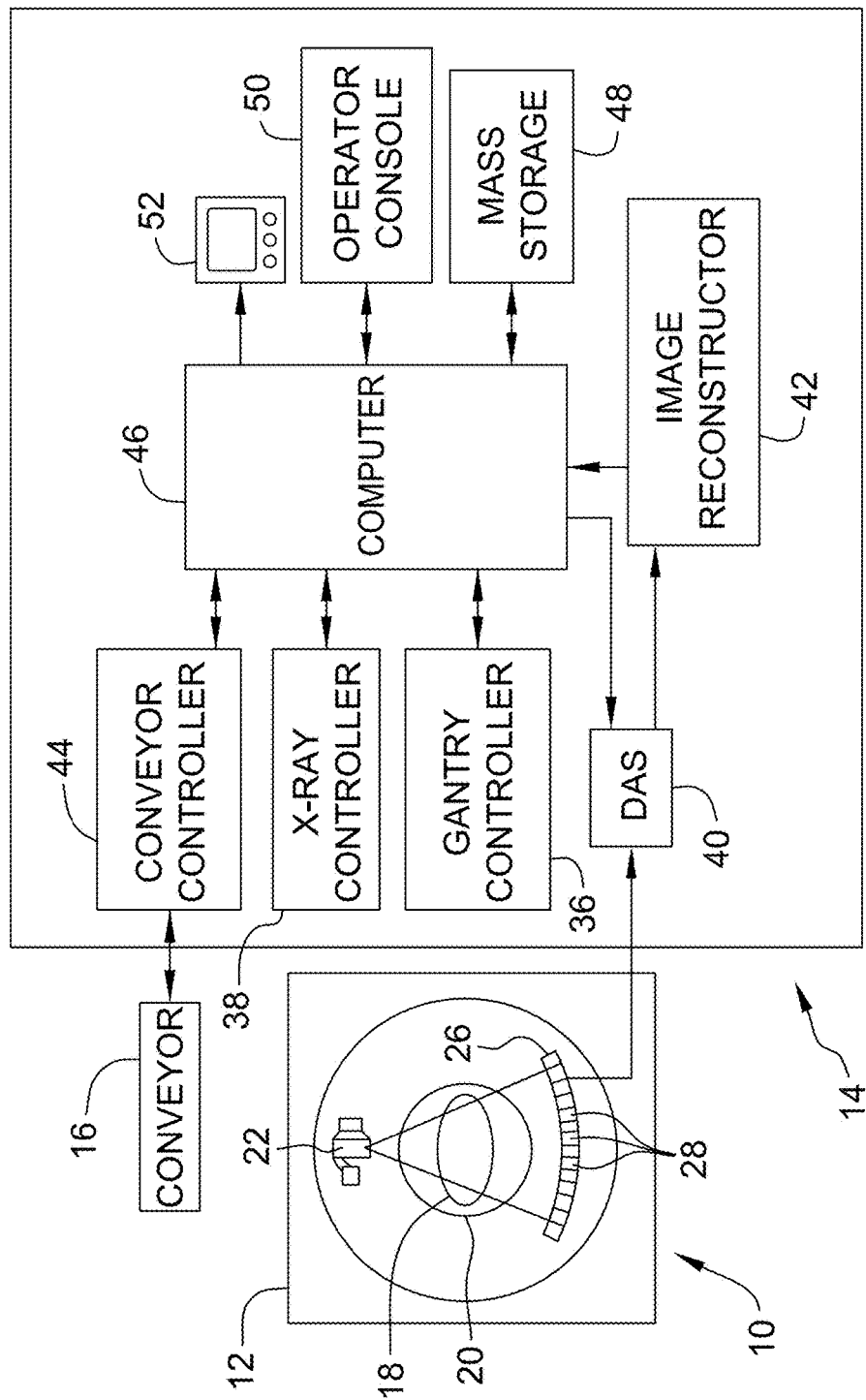
FIG. 2 is a schematic diagram of the CT imaging system shown in FIG. 1.

Referring now to FIGS. 1 and 2, a computed tomography (CT) imaging system 10 is shown. CT imaging system 10 is shown having a gantry 12, which is representative of a CT scanner, a control system 14, and a motorized conveyor belt 16 for positioning an object 18, such as a piece of luggage, in a gantry opening 20 defined through gantry 12. CT imaging system 10 may be, for example, a dual energy CT system. Gantry 12 includes an x-ray source 22 that projects a fan beam of x-rays 24 toward a detector array 26 on the opposite side of gantry 12. Detector array 26 is formed by detector elements 28, which are shown in more detail in FIG. 3 and discussed below. Detector elements 28 are radiation detectors that each produce a signal having a magnitude that represents and is dependent on the intensity of the attenuated x-ray beam after it has passed through object 18 being imaged. During a helical scan that acquires x-ray projection data, gantry 12 along with the x-ray source 22 and detector array 26 rotate within a plane and around object 18 about a center of rotation, while object 18 is moved through gantry 12 in a z-direction 32 perpendicular to the plane of rotation. In the exemplary embodiment, detector array 26 includes a plurality of detector rings each having a plurality of detector elements 28, the detector rings having an angular configuration corresponding to x-ray source 22.

Gantry 12 and x-ray source 22 are controlled by control system 14, which includes a gantry controller 36, an x-ray controller 38, a data acquisition system (DAS) 40, an image reconstructor 42, a conveyor controller 44, a computer 46, a mass storage system 48, an operator console 50, and a display device 52. Gantry controller 36 controls the rotational speed and position of gantry 12, while x-ray controller 38 provides power and timing signals to x-ray source 22, and data acquisition system 40 acquires analog data from detector elements 28 and converts the data to digital form for subsequent processing. Image reconstructor 42 receives the digitized x-ray data from data acquisition system 40 and performs an image reconstruction process that involves filtering the projection data using a helical reconstruction algorithm.

Computer 46 is in communication with the gantry controller 36, x-ray controller 38, and conveyor controller 44 whereby control signals are sent from computer 46 to controllers 36, 38, 44 and information is received from controllers 36, 38, 44 by computer 46. Computer 46 also provides commands and operational parameters to data acquisition system 40 and receives reconstructed image data from image reconstructor 42. The reconstructed image data is stored by computer 46 in mass storage system 48 for subsequent retrieval. An operator interfaces with computer 46 through operator console 50, which may include, for example, a keyboard and a graphical pointing device, and receives output, such as, for example, a reconstructed image, control settings and other information, on display device 52.

Communication between the various system elements of FIG. 2 is depicted by arrowhead lines, which illustrate a means for either signal communication or mechanical operation, depending on the system element involved. Communication amongst and between the various system elements may be obtained through a hardwired or a wireless arrangement. Computer 46 may be a standalone computer or a network computer and may include instructions in a variety of computer languages for use on a variety of computer platforms and under a variety of operating systems. Other examples of computer 46 include a system having a microprocessor, microcontroller or other equivalent processing device capable of executing commands of computer readable data or program for executing a control algorithm. In order to perform the prescribed functions and desired processing, as well as the computations therefore (e.g., the execution of Fourier analysis algorithm(s), the control processes prescribed herein, and the like), computer 46 may include, but not be limited to, a processor(s), memory, storage, register(s), timing, interrupt(s), communication interfaces, and input/output signal interfaces, as well as combinations including at least one of the foregoing. For example, computer 46 may include input signal filtering to enable accurate sampling and conversion or acquisitions of such signals from communications interfaces. As described above, exemplary embodiments can be implemented through computer-implemented processes and apparatuses for practicing those processes.

Figure 3:
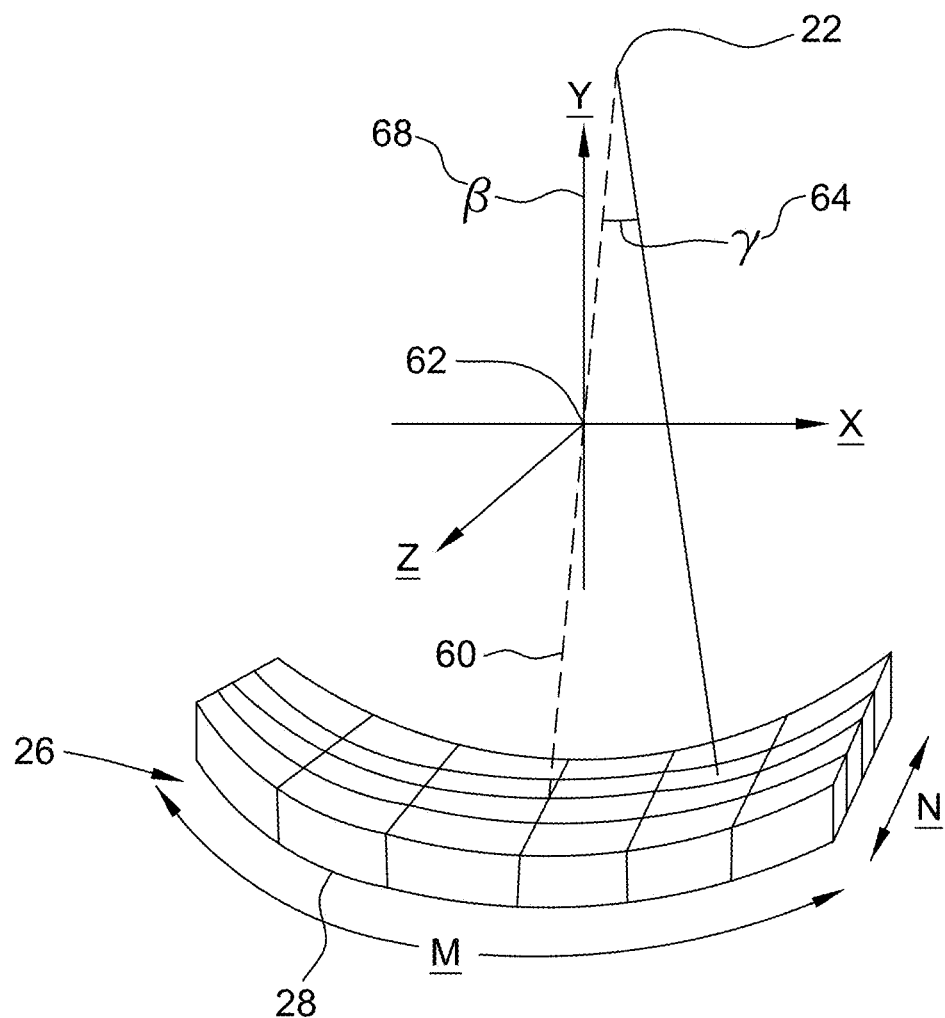
FIG. 3 is a schematic diagram of a detector array that may be used with the CT imaging system shown in FIG. 1.

Referring now to FIG. 3, an illustration of an x-ray beam having a beam axis (iso-ray) 60 that originates at x-ray source 22 and passes through center of rotation (iso-center) 62, relative to two-dimensional detector array 26, having detector elements 28 arranged in rows N and columns M, is provided. While FIG. 3 depicts only four rows (N=4 for four rings) and six columns (M=6 for six detectors per ring), it will be appreciated that any number of rows and columns may be employed as a matter of design choice. As depicted in FIG. 3, a detector angle γ 64 is shown as an angle formed between an x-ray intersecting a given detector element 28 and iso-ray 60 which connects x-ray source 22 and the iso-center 62, and a projection angle β 68 is shown as an angle formed by iso-ray 60 with the y-axis.

Figure 4:
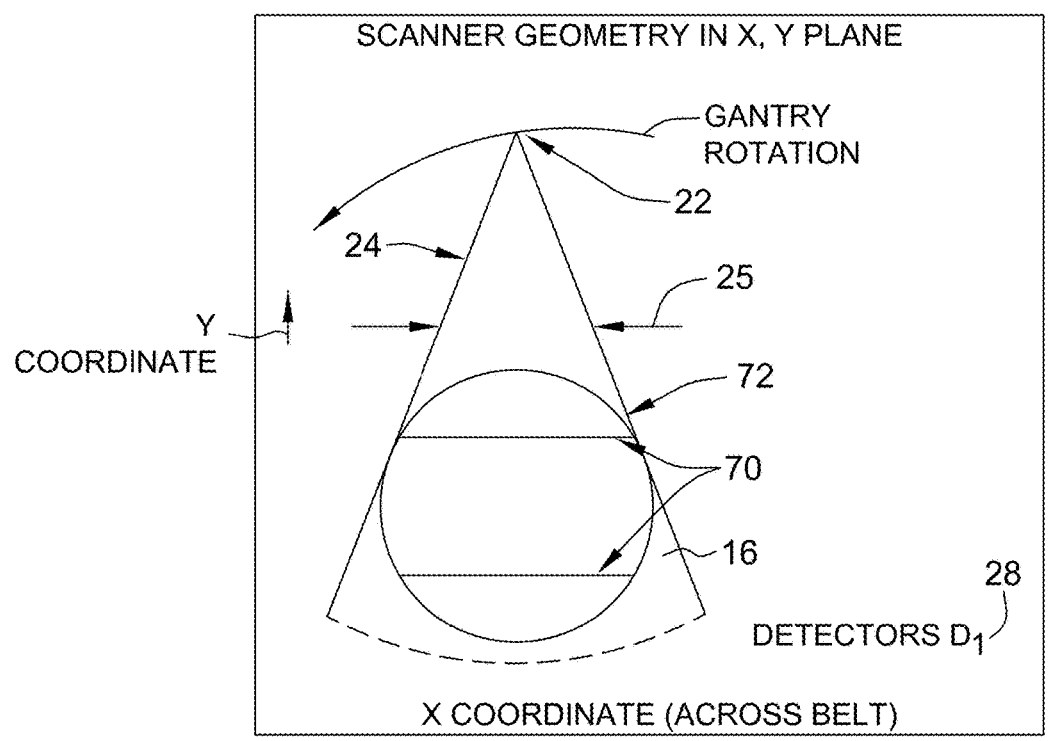
FIG. 4 is a schematic diagram of the geometry of the CT imaging system shown in FIG. 1.
Figure 5:
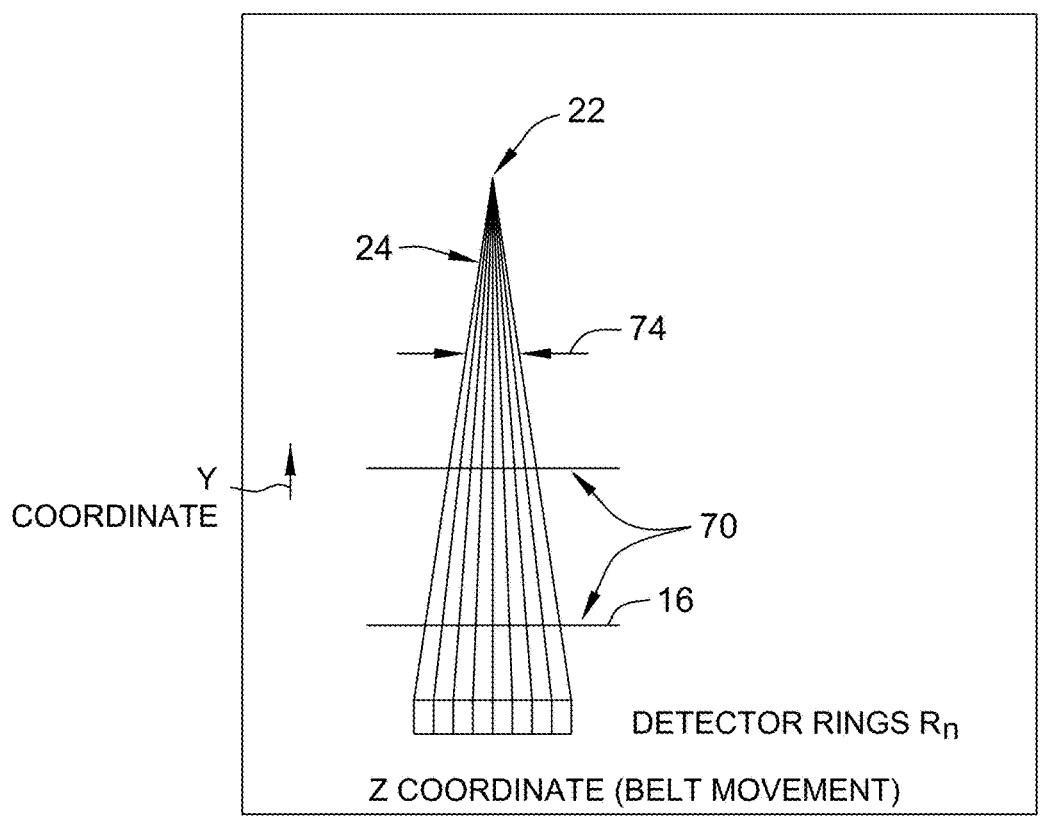
FIG. 5 is a schematic diagram of the geometry of the CT imaging system shown in FIG. 1.

Referring now to FIGS. 4 and 5, and in accordance with the exemplary embodiment, the data acquired at a single x-ray source position (also referred to herein as a view or tube position) is a set of fan beams 24 corresponding to a fan angle 25, with each x-ray beam at a slight angle to its neighbor. Also illustrated in FIGS. 4 and 5 is the bag or object volume 70, conveyor belt 16, a reconstruction circle 72, and a cone angle 74.

The systems and methods described herein facilitate determining a signature of object 18, in addition to reconstructing an image of object 18. This is achieved by blocking at least a portion of x-ray beam 24 such that a subset of detector elements 28 do not receive any direct incident radiation. In the exemplary embodiment, this is accomplished using a precollimator, as described herein. The detectors in the subset detect x-rays that have been scattered by object 18, and accordingly, are referred to herein as scatter detectors.

Figure 6:
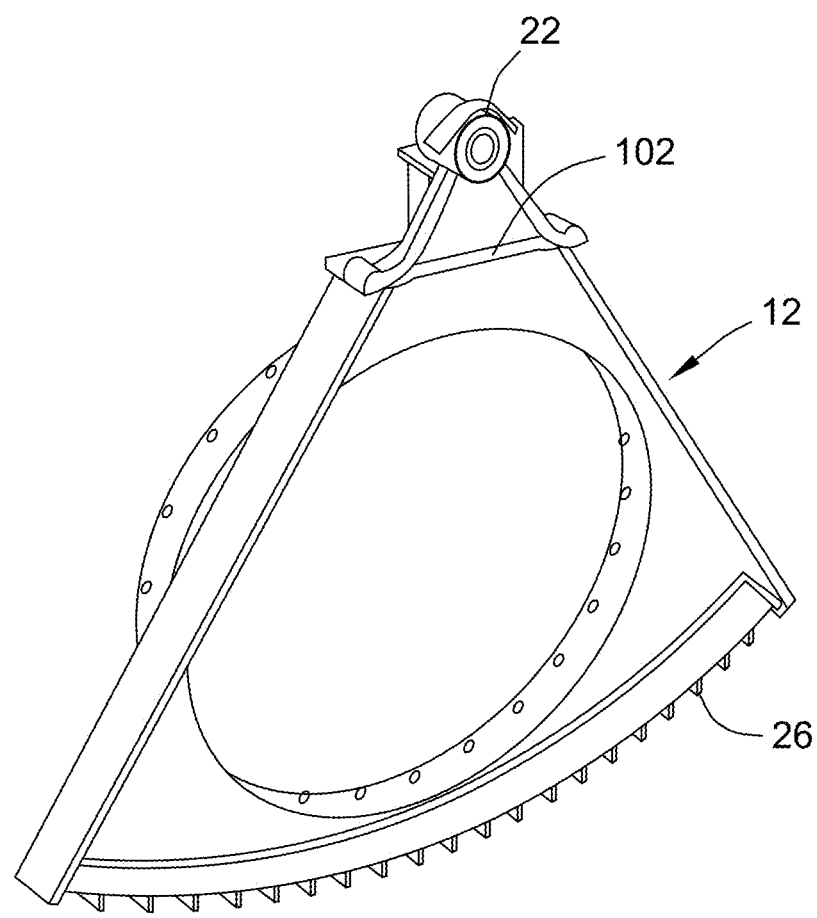
FIG. 6 is a perspective view of a portion of an exemplary gantry that may be used with the CT imaging system shown in FIG. 1.

FIG. 6 is a perspective view of a portion of gantry 12 (shown in FIG. 1). As show in FIG. 6, gantry 12 includes a precollimator 102 positioned between x-ray source 22 and detector array 26. Precollimator 102 blocks at least a portion of x-rays 24 emitted from x-ray source 22, as described herein.

Figure 7:
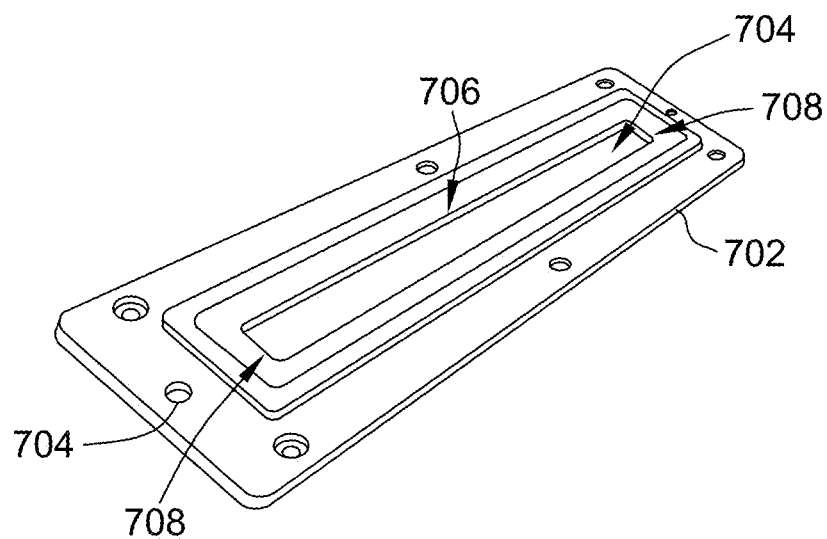
FIG. 7 is a perspective view of an exemplary precollimator that may be used with the CT imaging system shown in FIG. 1.

FIG. 7 is a perspective view of an exemplary precollimator 702. Precollimator 702 includes a plurality of apertures 704 that facilitate mounting precollimator 702 to gantry 12 using fastening devices (e.g., bolts). As shown in FIG. 7, precollimator 702 includes an aperture 704 defined therethrough. Aperture 704 enables substantially all x-rays 24 emitted from x-ray source 22 to pass therethrough. Accordingly, because precollimator 702 does not block any x-rays 24, detector array 26 does not include any scatter detectors when using precollimator 702. Aperture 704 is narrower at a midpoint 706 than at ends 708. Accordingly, aperture may have a bowed rectangular shape.

Figure 8:
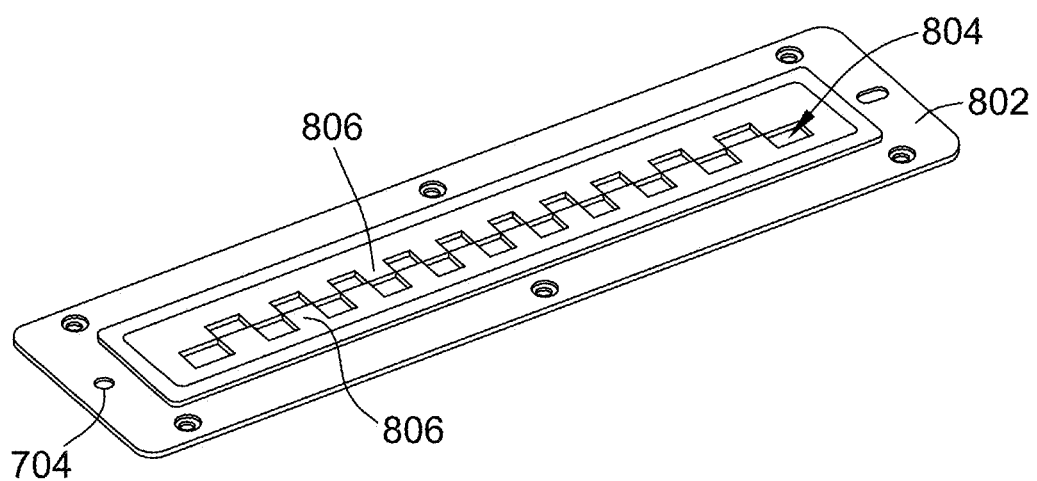
FIG. 8 is a perspective view of an exemplary precollimator that may be used with the CT imaging system shown in FIG. 1.

In contrast, FIG. 8 is a perspective view of an exemplary precollimator 802 that may be used with gantry 12. As shown in FIG. 8, an aperture 804 of precollimator 802 is substantially different than aperture 704 of precollimator 702. Specifically, aperture 804 includes a plurality of blocking portions 806 arranged in an alternating pattern to block sections of aperture 804. Accordingly, detector elements 28 in detector array 26 that are aligned with blocking portions 806 will not receive direct incident radiation and, accordingly, are scatter detectors. In the exemplary embodiment, blocking portions 806 are fabricated from tungsten. Alternatively, blocking portions 806 may be fabricated from any material that enables precollimator 802 to function as described herein.

The pattern of blocking portions 806 is merely an example. That is, blocking portions 806 may have any orientation and/or configuration that enables gantry 12 to function as described herein. In some embodiments, blocking portions 806 are arranged such that detector elements 28 in detector array 26 that would otherwise receive relatively little incident radiation are used as the scatter detectors.

Figure 9:
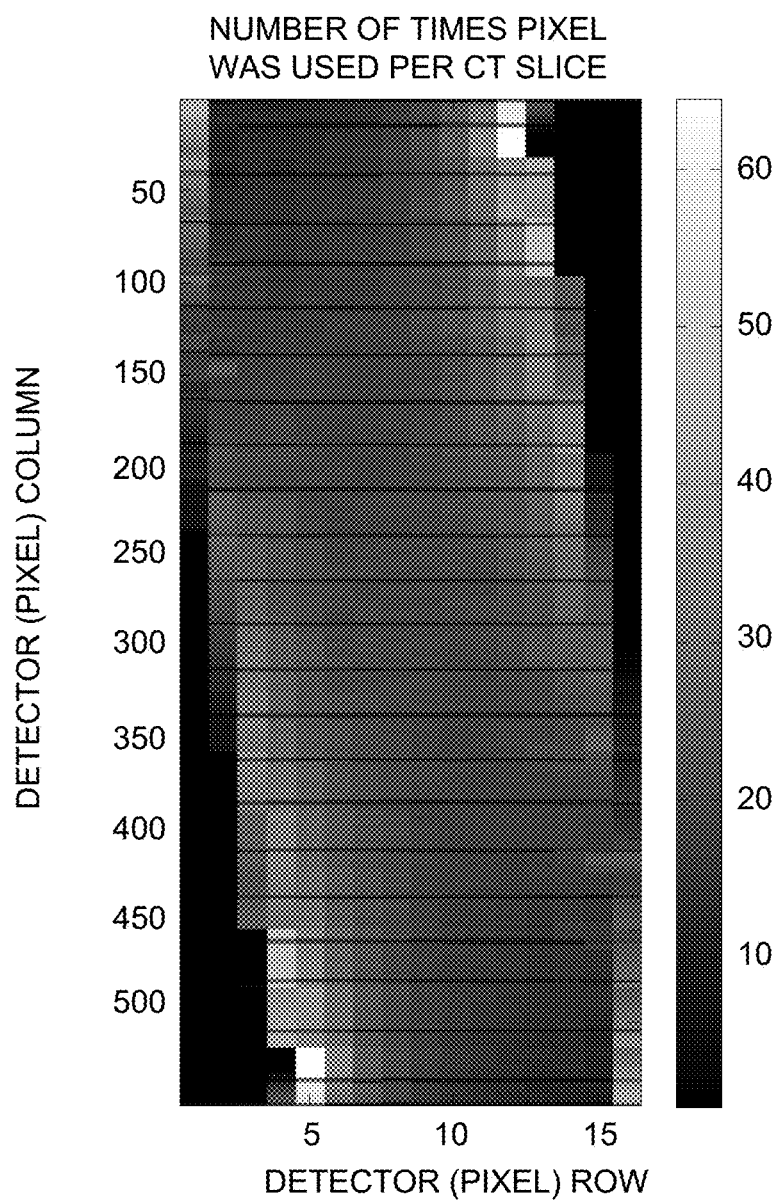
FIG. 9 is a diagram demonstrating how often each detector element in a detector array is used for reconstructing a the CT volume in a helical scan.

For example, FIG. 9 is a diagram 900 demonstrating how often each detector element 28 in detector array 26 is used for reconstructing a given CT volume in a helical scan without any blocking portions 806 (i.e., with all detector elements 28 receiving direct radiation). As shown in FIG. 9, detector elements 28 in a lower left corner of diagram 900 and detector elements 28 in an upper right corner of diagram 900 are used the least.

Figure 10:
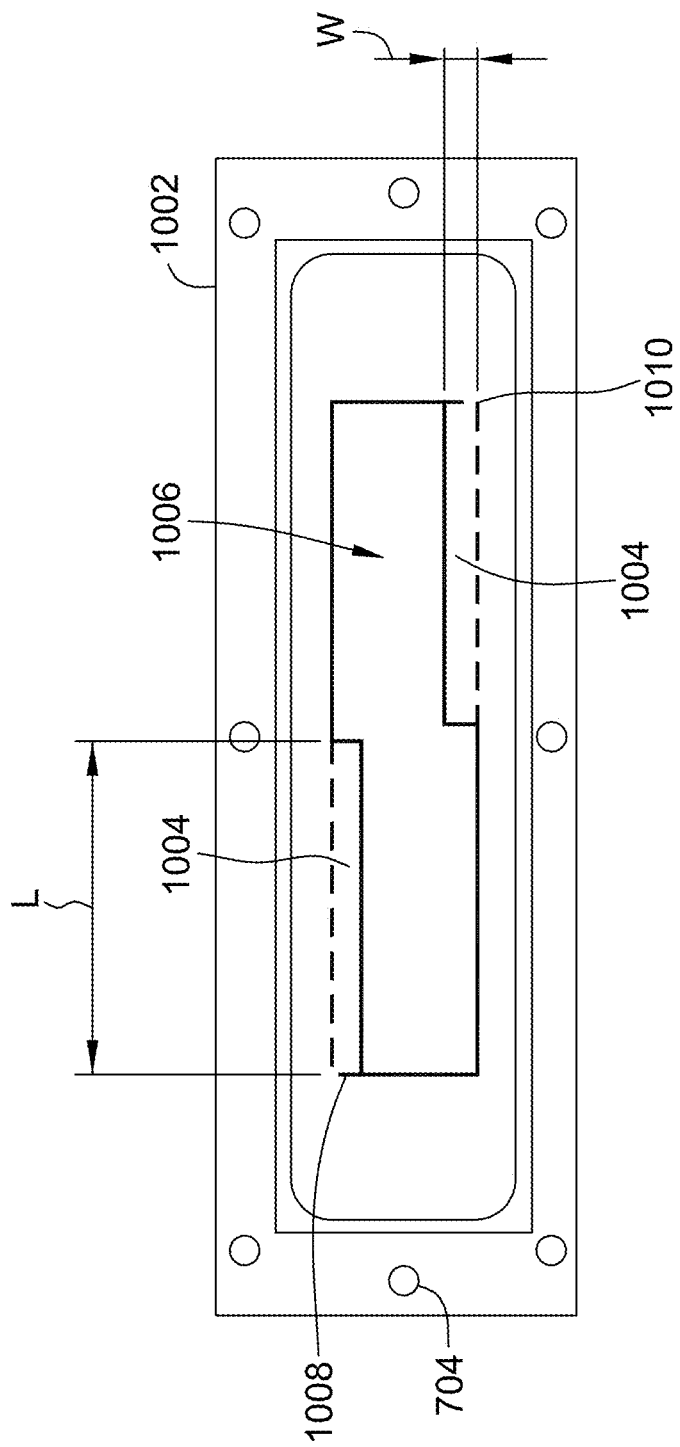
FIG. 10 is a schematic plan view of an exemplary precollimator that may be used with the CT imaging system shown in FIG. 1.

FIG. 10 is a schematic plan view of an exemplary precollimator 1002 designed based on diagram 900. Precollimator 1002 includes two blocking portions 1004 that block portions of aperture 1006. One blocking portion 1004 extends from a first corner 1008 of aperture 1006, and the other blocking portion 1004 extends from a second, opposite, corner 1010 of aperture 1006. In the exemplary embodiment shown in FIG. 10, each blocking portion 1004 has a length, L, extending from an associated corner 1008 and 1010 to a midpoint of aperture 1006. Further, each blocking portion has a width, W. In the exemplary embodiment, width W is a distance of approximately three to four detector rows. Alternatively, blocking portions 1004 may have any dimensions that enable precollimator 1002 to function as described herein.

Figure 11:
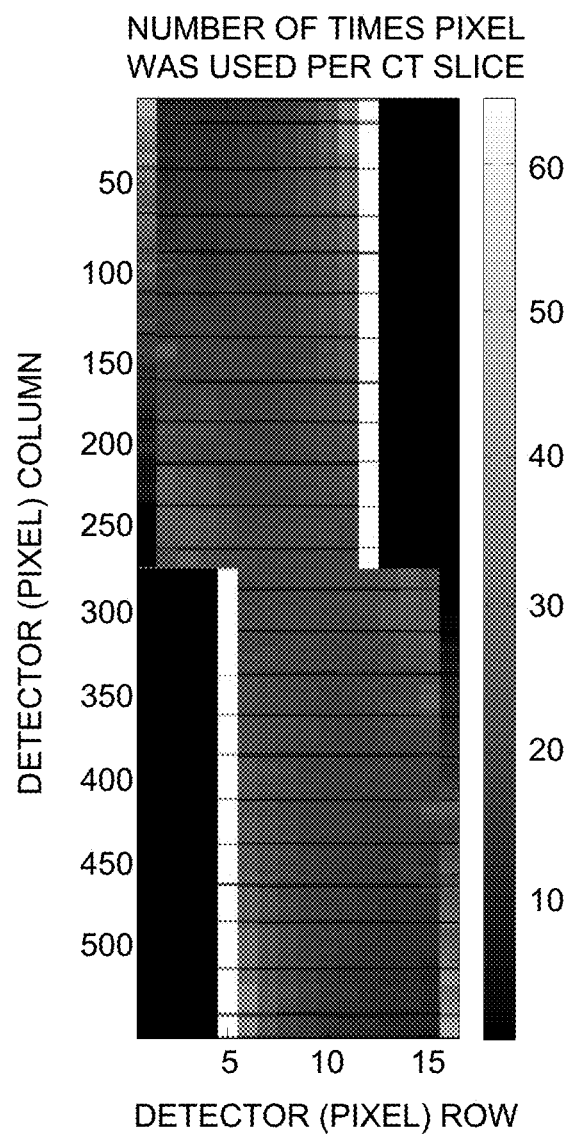
FIG. 11 is a diagram demonstrating how often each detector element in a detector array is used for reconstructing the CT volume in a helical scan using a rebinning algorithm.

In the systems and methods described herein, data acquired at detector elements 28 that receive direct incident radiation (i.e., unblocked detector elements) is used to tomographically reconstruct an image of object 18. Further, data acquired at detector elements 28 that do not receive direct incident radiation (i.e., scatter detectors) is used to calculate a signature of object 18. To avoid using data from the scatter detectors for image reconstruction, a rebinning algorithm is implemented. FIG. 11 is a diagram 1100 demonstrating how often detector elements 28 are used for reconstructing a given CT volume when using precollimator 1002 and an exemplary rebinning algorithm. Although an image of object 18 is reconstructed using less than all of detector elements 28, the image quality remains substantially unchanged.

To facilitate limiting the amount of data acquired by the scatter detectors, in the exemplary embodiment, detector array 26 includes collimator plates that extend parallel to at least one of rows and columns of detector elements 28. In some embodiments, because the fan angle is typically much larger than the cone angle, the collimator plates extend parallel to the columns of detector elements 28. This configuration is advantageous, as it rejects a significant amount of unwanted scatter photons. The data acquired by the scatter detectors is processed (e.g., using computer 46 (shown in FIG. 2)) to tomographically reconstruct a scatter function for object 18. The scatter function is a scatter cross section as a function of momentum transfer. In the exemplary embodiment, the scatter function is reconstructed only when object 18 has been identified as a potential threat (e.g., by applying an automated detection algorithm on the reconstructed image of object 18). Alternatively, the scatter function may be reconstructed for object 18 regardless of whether object 18 is previously identified as a potential threat. In the exemplary embodiment, for the scatter function reconstruction, it is assumed that object 18 consists of the same material (or material mix) throughout.

In the exemplary embodiment, to reconstruct the scatter function, a forward matrix is formed by identifying possible scatter events that link a voxel in object 18 to one of the scatter detectors. For each such event, a scatter angle is computed, an incident energy spectrum at the voxel and at the scatter detector is estimated, and the contribution to the measurement at the scatter detector is estimated for each basis component of an unknown scatter function. Collimator configurations, such as those described above, are taken into consideration to limit possible detected scatter paths.

Once an entire forward matrix is established (focusing on object 18 and any additional interfering objects), each scatter detector measurement is written as an equation as a function of parameters in the unknown scatter function. There will generally be many more equations than unknowns in the scatter function representation, so a minimum least-square solution for the scatter function may be possible. Iterative solutions with various types of regularization may also be implemented.

In the exemplary embodiment, the scatter function may be represented by a product of a first scatter function that ignores interactions between atoms and a second, molecular scatter function that takes into account interactions between atoms. The first scatter function is a function of atomic number and momentum transfer, and may be chosen based on an estimated effective atomic number calculated, for example, based on the reconstruction image. Accordingly, only the second, molecular scatter function, which extends in a lower range of a momentum transfer scale (e.g., up to 0.25 $\text{Å}^{-1}$), remains as an unknown.

As there will be a plurality of views that transect object 18 as gantry 12 rotates around object 18, data acquired at views that include relatively little amounts of interference (e.g., from additional objects) may be utilized to form the forward matrix. Further, if certain views contain relatively high amounts of interference, data acquired from those views may be omitted entirely.

Once the scatter function is reconstructed, a signature of object 18 may be determined based on the scatter function. For example, computer 46 may compare the scatter function with a library of predetermined scatter functions stored in mass storage system 48 to determine the signature (i.e., identifying the material) of object 18. The determined signature may be displayed to an operator on display device 52. Further, if the determined signature indicates a contraband material (e.g., an explosive or narcotic material), computer 46 may generate an alarm to alert the operator. As used herein, the "signature" may be a molecular signature (e.g., if object 18 is composed of a single type of molecule) or may be a more general signature that represents a mix of the molecular signatures corresponding to different types of molecules that constitute object 18.

Accordingly, the systems and methods described herein provide a CT imaging system that is capable of reconstructing an image of an object and determining a signature of the object. By determining a signature in addition to imaging the object, contraband detection may be improved and false alarms may be reduced.

The systems and methods described herein may be used to detect contraband. As used herein, the term "contraband" refers to illegal substances, explosives, narcotics, weapons, special nuclear materials, dirty bombs, nuclear threat materials, a threat object, and/or any other material that a person is not allowed to possess in a restricted area, such as an airport. Contraband may be hidden within a subject (e.g., in a body cavity of a subject) and/or on a subject (e.g., under the clothing of a subject). Contraband may also include objects that can be carried in exempt or licensed quantities intended to be used outside of safe operational practices, such as the construction of dispersive radiation devices.

A computer, such as those described herein, includes at least one processor or processing unit and a system memory. The computer typically has at least some form of computer readable media. By way of example and not limitation, computer readable media include computer storage media and communication media. Computer storage media include volatile and nonvolatile, removable and nonremovable media implemented in any method or technology for storage of information such as computer readable instructions, data structures, program modules, or other data. Communication media typically embody computer readable instructions, data structures, program modules, or other data in a modulated data signal such as a carrier wave or other transport mechanism and include any information delivery media. Those skilled in the art are familiar with the modulated data signal, which has one or more of its characteristics set or changed in such a manner as to encode information in the signal. Combinations of any of the above are also included within the scope of computer readable media.

Exemplary embodiments of methods and systems for imaging an object are described above in detail. The methods and systems are not limited to the specific embodiments described herein, but rather, components of systems and/or steps of the methods may be utilized independently and separately from other components and/or steps described herein. Accordingly, the exemplary embodiment can be implemented and utilized in connection with many other applications not specifically described herein.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An X-ray CT scanner for imaging an object, said X-ray CT scanner comprising:
    an X-ray emitter configured to emit X-ray beams towards the object;

a detector array positioned opposite said X-ray emitter and comprising a plurality of detector elements;

a precollimator positioned between said X-ray emitter and the object, said precollimator configured to:
  prevent, using at least one blocking portion, the emitted X-ray beams from being directly incident on a first subset of said plurality of detector elements; and
  allow the emitted X-ray beams to be directly incident on a second subset of said plurality of detector elements; and a processing device communicatively coupled to said detector array, said processing device configured to:
  determine a signature of the object based on a first set of data acquired using said first subset of said plurality of detector elements; and
  tomographically reconstruct an image of the object based on a second set of data acquired using said second subset of said plurality of detector elements.

2. An X-ray CT scanner in accordance with claim 1, wherein an aperture is defined through said precollimator, and wherein said at least one blocking portion comprises:
  a first blocking portion extending from a first corner of the aperture; and
  a second blocking portion extending from a second corner of the aperture.

3. An X-ray CT scanner in accordance with claim 1, wherein said at least one blocking portion comprises a plurality of blocking portions arranged in an alternating pattern.

4. An X-ray CT scanner in accordance with claim 1, wherein said processing device is further configured to:
  compare the determined signature to a plurality of predetermined signatures; and
  generate an alarm when the comparison indicates that the signature is indicative of contraband.

5. An X-ray CT scanner in accordance with claim 1, wherein said detector array comprises a plurality of collimators extending in at least one of a fan beam direction and a cone beam direction.

6. An X-ray CT scanner in accordance with claim 1, wherein to determine a signature of the object, said processing device is configured to reconstruct a scatter function for the object.

7. An X-ray CT scanner in accordance with claim 1, wherein said X-ray CT scanner is a helical CT scanner.

8. A method for imaging an object, said method comprising:
  positioning the object between an X-ray emitter and a detector array that includes a plurality of detector elements;
  emitting X-ray beams towards the object from the X-ray emitter;
  preventing, using a precollimator including at least one blocking portion, the emitted X-ray beams from being directly incident on a first subset of the plurality of detector elements;
  allowing the emitted X-ray beams to be directly incident on a second subset of the plurality of detector elements;
  determining, using a processing device communicatively coupled to the detector array, a signature of the object based on a first set of data acquired using the first subset of the plurality of detector elements; and
  tomographically reconstructing, using the processing device, an image of the object based on a second set of data acquired using the second subset of the plurality of detector elements.

9. A method in accordance with claim 8, wherein preventing the emitted X-ray beams from being directly incident on a first subset of the plurality of detector elements comprises preventing the emitted X-ray beams from being directly incident on the first subset using a precollimator that includes a first blocking portion extending from a first corner of an aperture defined through the precollimator, and a second blocking portion extending from a second corner of the aperture.

10. A method in accordance with claim 8, wherein preventing the emitted X-ray beams from being directly incident on a first subset of the plurality of detector elements comprises preventing the emitted X-ray beams from being directly incident on the first subset using a precollimator that includes a plurality of blocking portions arranged in an alternating pattern.

11. A method in accordance with claim 8, further comprising:
  comparing, using the processing device, the determined signature to a plurality of predetermined signatures; and
  generating, using the processing device, an alarm when the comparison indicates that the signature is indicative of contraband.

12. A method in accordance with claim 8, wherein positioning the object between an X-ray emitter and a detector array comprises positioning the object between the X-ray emitter and a detector array that includes a plurality of collimators extending in at least one of a fan beam direction and a cone beam direction.

13. A method in accordance with claim 8, wherein determining a signature of the object comprises reconstructing a scatter function for the object.

14. A method of assembling an X-ray CT scanner for imaging an object, said method comprising:
  positioning an X-ray emitter opposite a detector array that includes a plurality of detector elements, the X-ray emitter configured to emit X-ray beams towards the object;
  positioning a precollimator between the X-ray emitter and the object, the precollimator including at least one blocking portion configured to:
    prevent the emitted X-ray beams from being directly incident on a first subset of the plurality of detector elements; and
    allow the emitted X-ray beams to be directly incident on a second subset of the plurality of detector elements; and
  communicatively coupling a processing device to the detector array, the processing device configured to:
    determine a signature of the object based on a first set of data acquired using the first subset of the plurality of detector elements; and
    tomographically reconstruct an image of the object based on a second set of data acquired using the second subset of the plurality of detector elements.

15. A method in accordance with claim 14, wherein positioning a precollimator comprises positioning a precollimator that includes a first blocking portion extending from a first corner of an aperture defined through the precollimator, and a second blocking portion extending from a second corner of the aperture.

16. A method in accordance with claim 14, wherein positioning a precollimator comprises positioning a precollimator that includes a plurality of blocking portions arranged in an alternating pattern.

17. A method in accordance with claim 14, wherein communicatively coupling a processing device comprises communicatively coupling a processing device that is further configured to:
   compare the determined signature to a plurality of predetermined signatures; and
   generate an alarm when the comparison indicates that the signature is indicative of contraband.

18. A method in accordance with claim 14, wherein positioning an X-ray emitter opposite a detector array comprises positioning the X-ray emitter opposite a detector array that includes a plurality of collimators extending in at least one of a fan beam direction and a cone beam direction.

19. A method in accordance with claim 14, wherein positioning an X-ray emitter opposite a detector array comprises positioning the X-ray emitter opposite a detector array including a plurality of rows and a plurality of columns.

20. A method in accordance with claim 14, wherein communicatively coupling a processing device comprises communicatively coupling a processing device that is configured to determine a signature of the object by reconstructing a scatter function for the object.

\* \* \* \* \*